US005707824A

United States Patent [19]
Felder et al.

[11] Patent Number: 5,707,824
[45] Date of Patent: Jan. 13, 1998

[54] METHOD OF DETERMINING THE PRESENCE OR ABSENCE OF A PARAFFINOPHILIC MICROORGANISM

[75] Inventors: Mitchell S. Felder, Hermitage; Robert A. Ollar, Milford, both of Pa.

[73] Assignee: Infectech, Inc., Sharon, Pa.

[21] Appl. No.: 555,734

[22] Filed: Nov. 9, 1995

[51] Int. Cl.$^6$ .................... C12Q 1/04; C12Q 1/24
[52] U.S. Cl. .................... 435/34; 435/30; 435/863
[58] Field of Search .................... 435/30, 34, 36, 435/40, 287.9, 288.1, 288.3, 801, 863

[56] References Cited

U.S. PATENT DOCUMENTS

| | | | |
|---|---|---|---|
| 3,826,717 | 7/1974 | Gilbert et al. | 195/103.5 R |
| 4,683,195 | 7/1987 | Mullis et al. | 435/6 |
| 4,683,201 | 7/1987 | Hamill et al. | 435/75 |
| 4,683,202 | 7/1987 | Mullis | 435/91 |
| 4,692,407 | 9/1987 | Jordan et al. | 435/36 |
| 5,153,119 | 10/1992 | Ollar | 435/34 |
| 5,316,918 | 5/1994 | Ollar | 435/34 |
| 5,472,877 | 12/1995 | Ollar | 435/288.1 |

OTHER PUBLICATIONS

Hambleton R., A Study of the Effect of Carbon Dioxide on the Germination and Outgrowth of Sproes of Clostridium butyricum Using a Slide Culture Technique, J of Applied Bacteriology 33(4) 664–673 Dec. 1970.
Weinstein M., Controlled Evaluation of Trypticase Soy Broth in Agar Slide and Conventional Blood Culture Systems, J of Clinical Micro 21(4) 626–629 Apr. 1985.
Wallace et al., *Chest*, 93(5) 926–932 (1988).
Wolinsky, *American Review Of Respiratory Disease*, vol. 119:107–159 (1979).
Horsburgh, Jr. et al., *Medicine*, vol. 64, No. 1: 36–48 (1983).
Horsburgh, Jr. et al., *American Review Of Respiratory Disease*, 139: 4–7 (1989).
C.M. Reichert et al., *Aids: Etiology, Diagnosis, Treatment And Prevention*, p. 134, Lippencott (1985).
C.C. Hawkins et al., *Annals Of Internal Medicine*, 105: pp. 184–188 (1986).
J. Hoy et al, *The Journal Of Infectious Diseases*, 161:801–805 (1990).
Fuhs, G.W., *Arch Mikrobiol*, 39: 374–422 (1961) (German).
Mishra, S.K. et al., *Mycopathologia Et Mycologia Applicata*, vol. 51 (2–3): 147–157 (1973).
Ollar, *Zbl. Bakt. Hyg. 1.Abt. Orig. A 234*: 81–90 (1976).
Kemper et al., *American Society For Microbiology*, 297 (Abstract) (1990).
Klatt et al., *Human Pathology*, vol. 18, No. 7: 709–714 (1987).
Bermudez et al., *The Journal Of Infectious Diseases*, 165: 75–79 (1992).
Murphy et al., *American Society For Microbiology*, 277 (1983) Abstract.
P. Ma et al., *Aids And Infections Of Homosexual Men*, 233–234 (1989).
Havlik Jr. et al., *The Journal Of Infectious Diseases*, 165: 577–580 (1992).
Inderlied et al., *Aids Clinical Review*, 165–191 (1990).
Gonzalez et al., *Diagn. Microbiol. Infect. Dis.* 8: 69–77 (1987).
Ollar et al., *Tubercle*, 71, pp. 23–28 (1990).

(List continued on next page.)

*Primary Examiner*—Ralph Gitomer
*Attorney, Agent, or Firm*—David V. Radack; Eckert Seamans Cherin & Mellott, LCC

[57] ABSTRACT

A method of determining the presence of a paraffinophilic microorganism in a specimen taken from a patient is provided. The method includes providing a receptacle containing an aqueous solution and adjusting the solution to mimic the in vivo clinical conditions of the patient. The method then further includes inoculating the solution with the specimen and then placing in the receptacle a paraffin coated slide to bait the paraffinophilic microorganism. The slide is then analyzed after exposure to the specimen to determine the presence or absence of the paraffinophilic microorganism. An associated apparatus is also disclosed.

6 Claims, 1 Drawing Sheet

OTHER PUBLICATIONS

Kemper et al., *Annals Of Internal Medicine*, 116: 466–472 (1992).

Heifets et al., *Antimicrobial Agents And Chemotherapy*, 1298–1301 (1989).

Hurley et al., *Journal Of Clinical Microbiology*, pp. 1582–1587 (1989).

Kirihara et al., *Journal Of Clinical Microbiology*, pp. 841–845 (1985).

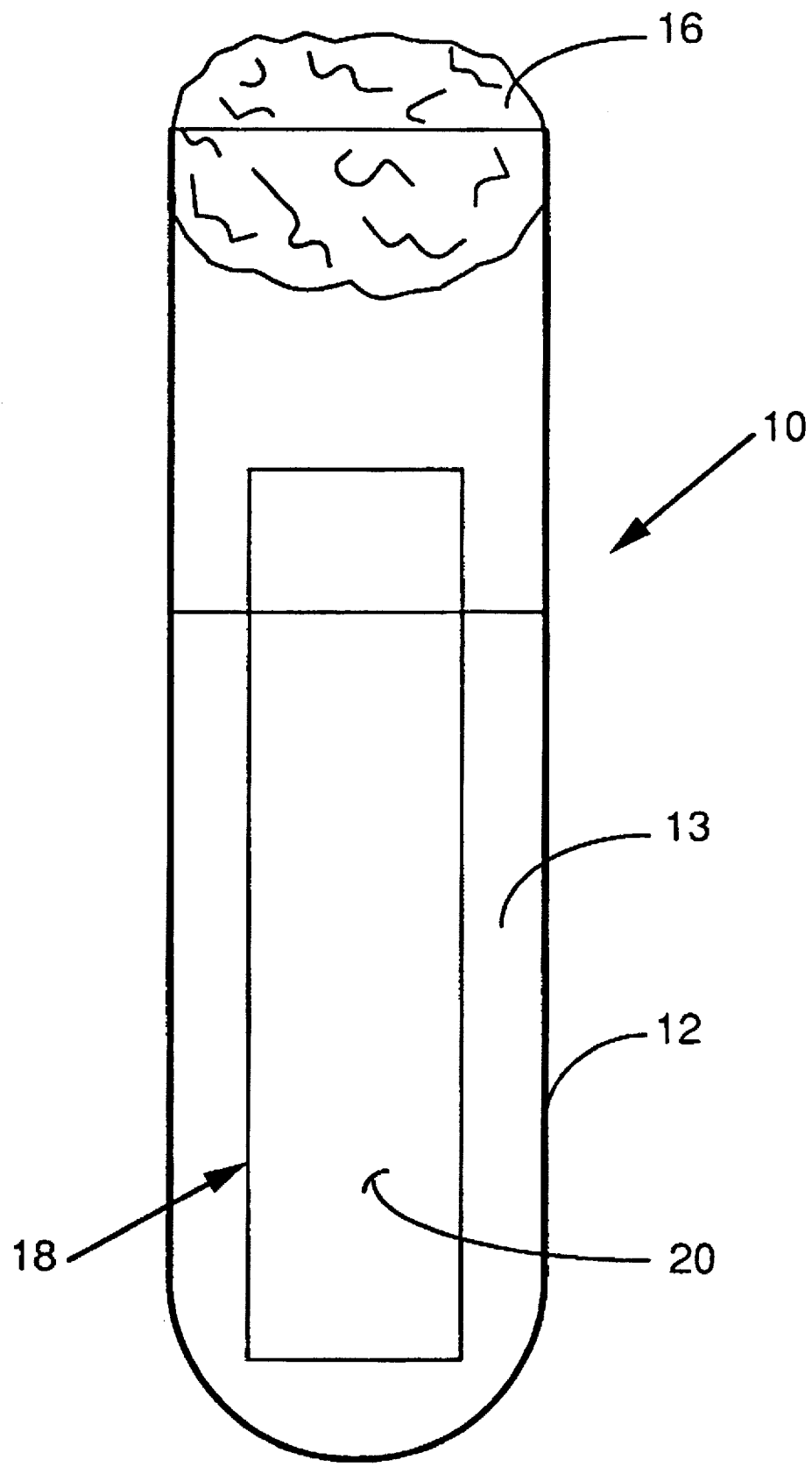

METHOD OF DETERMINING THE PRESENCE OR ABSENCE OF A PARAFFINOPHILIC MICROORGANISM

BACKGROUND OF THE INVENTION

This invention relates to a method of identifying a paraffinophilic microorganism using various milieus and an associated apparatus and, more particularly, to a receptacle containing an aqueous solution that mimics the in vivo conditions of a patient. A paraffin coated slide is used to bait a paraffinophilic organism that can grow on the slide. The organism then can be identified by a number of different methods.

U.S. Pat. Nos. 5,153,119 and 5,316,918, the disclosures of which are incorporated by reference herein, disclose methods and apparatus for identifying and testing the antibiotic sensitivity of *Mycobacterium avium-intracellulare* ("MAI"). One of the co-inventors herein, Robert-A. Ollar, was the named inventor on these patents. The method of identifying MAI includes placing a paraffin coated slide in a receptacle containing a sterile aqueous solution inoculated with a specimen from a patient and analyzing the slide after exposure to the specimen to determine the presence or absence of MAI. The analysis step involves performing a number of speciation assays, such as a tellurite reduction test. The method for testing the sensitivity of MAI to different antimicrobial agents and dosages thereof includes providing a plurality of test tubes adapted to contain an amount of an antimicrobial agent to be tested and MAI to be assayed and a separate paraffin coated slide adapted for placement in each of the test tubes. Observing the growth of MAI on the slide can be used to determine the concentration of the antimicrobial agent necessary to resist MAI growth on the slide.

The inventions provide effective, efficient and economical methods for identifying MAI and testing MAI for antimicrobial agent sensitivity. These methods avoid the use of expensive, complicated equipment, and thus can be used in places such as field hospitals and third world locations where the more expensive and hard to use equipment is not available.

Despite the effectiveness of the methods and apparatus disclosed in the above-mentioned patents, it would be desired to refine the process of identifying MAI, as well as other paraffinophilic microorganisms.

SUMMARY OF THE INVENTION

The invention has met or surpassed the above-mentioned need as well as others. The method of determining the presence of a paraffinophilic microorganism in a specimen taken from a patient includes providing a receptacle containing an aqueous solution and adjusting the solution to mimic the in vivo clinical conditions of the patient. The method further includes inoculating the solution with the specimen and then placing in the receptacle a paraffin coated slide. The slide is then analyzed after exposure to the specimen to determine the presence or absence of the microorganism.

An apparatus to facilitate determination of the presence or a paraffinophilic microorganism in a specimen taken from a patient is also provided. The apparatus comprises a receptacle for holding an aqueous solution and a paraffin coated slide adapted to be placed in the receptacle. The apparatus further comprises means for adjusting the aqueous solution to mimic the in vivo clinical conditions of the patient.

BRIEF DESCRIPTION OF THE DRAWING

A full understanding of the invention can be gained from the following detailed description of the invention when read in conjunction with the accompanying lone drawing which shows a front elevational view of a test tube holding a paraffin coated slide in an aqueous solution inoculated with a specimen.

DETAILED DESCRIPTION

As used herein, the term "patient" refers to a member of the animal kingdom, including human beings whose body specimen is being processed by the method and apparatus of the invention.

As used herein, the term "paraffinophilic" means an organism that can employ paraffin as a source of carbon in a basal salt media, devoid of other forms of carbon, the organism can be bacterial or fungal in nature.

The method and apparatus of the invention provide an efficient, effective and economical way of identifying a paraffinophilic microorganism. Referring to the lone FIGURE, one embodiment of a paraffinophilic microorganism identification apparatus 10 is shown. The apparatus 10 includes a standard test tube 12 which contains an aqueous solution 13 (such as distilled water) and a cotton plug 16 to seal the test tube 12. A specimen to be tested for the presence or absence of a paraffinophilic microorganism is inoculated into the aqueous solution 13. A slide 18, having a coating of paraffin 20 is then placed into the test tube 12. It will be appreciated that the aqueous solution 13 should not contain any carbon source, as it is desired to provide a sole carbon source on the slide in order to effectively grow the microorganism to be identified on the slide 18 and not in the aqueous solution 13. Growth on the paraffin coated slide 18 can be analyzed to determine the presence or absence of a paraffinophilic microorganism. Such tests to analyze the growth can include tests such as DNA hybridization or can be tests for specific paraffinophilic microorganisms, such as MAI, as is disclosed in U.S. Pat. Nos. 5,153,119 and 5,316,918, the disclosures of which are specifically incorporated by reference herein.

The specimen to be inoculated into the test tube 12 can be a blood sample; any biopsy or tissue specimen; stomach fluid; urine; cerebral spinal fluid; nasopharyngeal mucosa or saliva. These specimens can be obtained from the patient in the doctor's office or in the emergency room of a hospital, for example, by known techniques in known standard ways.

The paraffin 20 included on the slide is used to bait the paraffinophilic microorganism. For example, the paraffin can be used to bait MAI. It will be appreciated that the aqueous solution 13 should not contain any carbon source, as it is desired to provide a sole carbon source on the slide in order to effectively identify the microorganism.

In accordance with the invention, the aqueous solution 13 can be adjusted to mimic the in vivo "clinical conditions" of the patient. By "clinical conditions" it is meant at least one of the following: (i) the pH of the in vivo milieu of the patient where the paraffinophilic microorganism can be found and (ii) the electrolyte levels of a patient's blood where paraffinophilic microorganisms can be found. Adjusting the aqueous solution can be effected by numerous different methods. Adjusting the pH of the aqueous solution can be accomplished by adding hydrochloric acid (HCl) to obtain a more acidic solution or by adding sodium hydroxide (NaOH) or potassium hydroxide (KOH) in order to obtain a more basic solution. Electrolytes such as one or more selected from the group consisting of sodium, potassium, chloride, magnesium, phosphate and calcium, can be added to the solution in desired quantities in order to mimic the electrolytes in the blood of a patient from which a blood sample which may contain the microorganism is obtained.

Paraffinophilic microorganisms that can be identified using the method of the invention include at least one of the paraffinophilic microorganisms selected from the group consisting of Micrococcus Paraffinae; Corynebacterium Simplex; Ahnl; Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei. M. Smegmatis; Mycobacterium Testudo; Mycobacterium-Avium-Intracellulare; Nocardia Spp.; Actinomyces; Candida Lipolytica; Candida Tropicalis, Torulopsis Colliculosa; *Monila Sp., Hansenula Sp., Torula rossa; Penicillium Sp.*; IHNL. Aspergillus Flavus; *Aspergillus sp., Penicillium Sp.; Citromyces Sp., Scopulariopsis Sp.*; Pseudomonas Fluorescens Liquefaciens; Ahnl, Pem. Fluorescens Denitrificans; Pseudomonas Aeruginosa.

EXAMPLE 1

An AIDS patient comes to an emergency room at a hospital complaining of severe abdominal pain. A gastroenterologist uses a gastrointestinal scope to obtain a specimen of the patient's stomach fluid. The scope indicates that the pH in the patient's stomach is 1.5. In the meantime, a lab technician using the apparatus of the FIGURE adjusts the pH of the aqueous solution 13 by adding HCl thereto so that the aqueous solution 13 has a pH of 1.5. Thus, the pH in the patient's stomach is mimicked by the pH of the aqueous solution in the apparatus shown in the FIGURE. After this, the specimen of stomach fluid taken by the gastroenterologist from the patient is inoculated into the receptacle 12 holding a paraffin coated slide 18. After about eight days a growth appears on the paraffin coated slide 18. The growth is then analyzed by the method and apparatus disclosed in U.S. Pat. No. 5,153,119 to determine whether MAI is present.

EXAMPLE 2

An AIDS patient comes to an emergency room complaining of high fever and apparently has pneumonia. The physician suspects that there is an infection caused by Nocardia bactereremia. As is standard in almost every emergency room, a chemical screen ("CSS") is performed on a blood specimen obtained from the patient. The CSS lists the electrolyte content of the patient's blood. The electrolyte content is communicated to a lab technician who in turn adjusts the aqueous solution 13 in the receptacle 12 holding the paraffin coated slide 18. For example, the CSS reveals that the patient has a sodium level of 120. The lab technician adjusts the sodium level of the aqueous solution (for example, distilled water) by adding sodium thereto in order to mimic the 120 level of sodium found in the patient's blood. The blood specimen is then inoculated into the adjusted aqueous solution. After about two days a growth appears. The growth is analyzed and is found to be, indeed, Nocardia bactereremia.

It will be appreciated that a method for identifying a paraffinophilic microorganism has been disclosed in which the aqueous solution in which the paraffin coated slide and the microorganism are placed is adjusted to mimic the in vivo clinical conditions of a patient from whom the specimen containing the paraffinophilic microorganism to be identified is obtained. The method is effective and efficient and does not involve the use of expensive and complicated equipment. An associated apparatus is also disclosed.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of determining the presence or absence of a paraffinophilic organism in a specimen taken from a patient having in vivo clinical conditions, said method comprising:

providing a receptacle containing an aqueous solution;

adjusting said aqueous solution to mimic said in vivo clinical conditions of said patient;

inoculating said solution with said specimen;

placing into said receptacle a paraffin coated slide; and observing said slide after exposure to said specimen to determine the presence or absence of said microorganism.

2. The method of claim 1, including said specimen is selected from the group consisting of blood, stomach fluid, urine, cerebral spinal fluid, nasopharyngeal mucosa and saliva.

3. The method of claim 1, including determining a pH of said specimen; and adjusting said aqueous solution to have a pH generally equal to said pH of said specimen.

4. The method of claim 1, including employing as said specimen a blood sample of said patient;

determining an electrolyte level of said blood sample; and adjusting said aqueous solution to have an electrolyte level generally equal to said electrolyte level of said patient's blood.

5. The method of claim 4, including adjusting said aqheous solution by adding thereto at least one of the group consisting of sodium, potassium, chloride, magnesium, phosphate and calcium.

6. The method of claim 1, including employing said method to determine the presence or absence of at least one member of the group consisting of Micrococcus Paraffinae; Corynebacterium Simplex; Ahnl; Mycococcus (Rhodococcus) Cinnabareus; Ahnl. Mycococcus (Rhodoc) Rhodochrous; Mycobact. Perrugosum Vat. Athanicum; Mycobact. Rubrum Vat. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.; Actinomyces; Candida Lipolytica; Candida Tropicalis, Torulopsis Colliculosa; *Monila Sp., Hansenula Sp., Torula rossa; Penicillium Sp.*; IHNL. Aspergillus Flayus; *Aspergillus sp., Penicillium Sp.; Citromyces Sp., Scopulariopsis Sp.*; Pseudomonas Fluorescens Liquefaciens; Ahnl, Pem. Fluorescens Denitrificans; Pseudomonas Aeruginosa.

* * * * *